United States Patent [19]

Binon et al.

[11] 3,984,470
[45] Oct. 5, 1976

[54] AMIDOXIME DERIVATIVES AND PROCESS FOR PREPARING THE SAME

[75] Inventors: Fernand Binon, Strombeek-Bever, Belgium; Pierre Luc Eymard, Fontaine, France

[73] Assignee: LABAZ, Paris, France

[22] Filed: July 28, 1975

[21] Appl. No.: 599,355

Related U.S. Application Data

[62] Division of Ser. No. 530,076, Dec. 6, 1974, Pat. No. 3,931,240.

[30] Foreign Application Priority Data

Jan. 15, 1974   France .............................. 74.01286

[52] U.S. Cl. .................... 260/564 G; 260/501.14; 424/316
[51] Int. Cl.² ...................................... C07C 123/00
[58] Field of Search .................... 260/564 G, 501.14

[56] References Cited
UNITED STATES PATENTS

| | | | |
|---|---|---|---|
| 3,139,455 | 6/1964 | Campbell | 260/564 G |
| 3,394,181 | 7/1968 | Bell | 260/564 G |
| 3,720,714 | 3/1973 | Bailey | 260/564 G |
| 3,723,527 | 3/1973 | Lafon | 260/564 G |
| 3,819,702 | 6/1974 | Lafon | 260/564 G |
| 3,855,249 | 12/1974 | Lafon | 260/564 G |

OTHER PUBLICATIONS
Chemical Abstracts, vol. 54, 12852(a).

*Primary Examiner*—Gerald A. Schwartz
*Attorney, Agent, or Firm*—Mason, Kolehmainen, Rathburn & Wyss

[57] ABSTRACT

Amidoxime derivatives corresponding to the general formula:

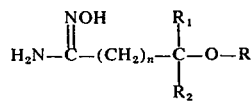

and pharmaceutically acceptable acid addition salts thereof, wherein $R_1$ and $R_2$, which are the same or different, represent hydrogen or a straight-chain lower alkyl radical containing from 1 to 3 carbon atoms, $n$ is 0, 1 or 2 and R is selected from the groups consisting of:

A=

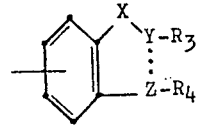

B=

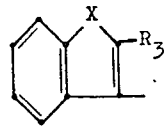

C=

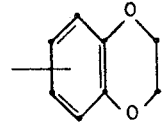

D= 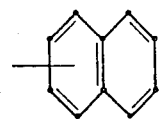

wherein X represents oxygen or sulphur, Y ... Z represents HC—CH or C=C, $R_3$ and $R_4$, which are the same or different, represent hydrogen or a branched- or straight-chain lower alkyl radical containing from 1 to 3 carbon atoms with the provisos that:
 a. when $n$ is 1, $R_1$ and $R_2$ are each hydrogen and R is selected from the groups A, B, C and D.
 b. when $n$ is 2, $R_1$ and $R_2$ area each hydrogen and R is selected from the groups A, B, C and the group D when it represents β-naphthyl.

They are effective as antidepressive and antiaggressive agents.

4 Claims, No Drawings

AMIDOXIME DERIVATIVES AND PROCESS FOR PREPARING THE SAME

This is a division of application Ser. No. 530,076, filed Dec. 6, 1974, now U.S. Pat. No. 3,931,240.

This invention relates to novel amidoxime derivatives having pharmacological activity and to a process for preparing the said novel amidoxime derivatives.

The amidoxime derivatives with which the invention is concerned can be represented by the general formula:

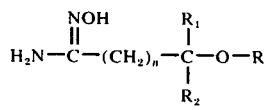    I wherein $R_1$ and $R_2$, which are the same or different, represent hydrogen or a straight-chain lower alkyl radical containing from 1 to 3 carbon atoms, $n$ is 0, 1 or 2 and R is selected from the groups consisting of:

A = 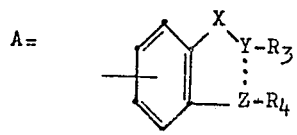

B = 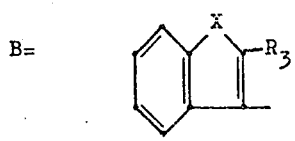

C = 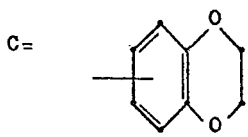

D = 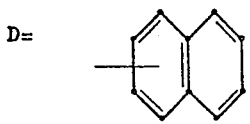

wherein X represents oxygen or sulphur, Y ... Z represents HC—CH or C=C, $R_3$ and $R_4$, which are the same or different, represent hydrogen or a branched- or straight-chain lower alkyl radical containing from 1 to 3 carbon atoms with the provisos that:

a. When $n$ is 1, $R_1$ and $R_2$ are each hydrogen and R is selected from the groups A, B, C and D.

b. When $n$ is 2, $R_1$ and $R_2$ are each hydrogen and R is selected from the groups A, B, C and the group D when the latter represents β-naphthyl.

The pharmaceutically acceptable acid addition salts of the compounds of formula I are also included within the scope of the invention.

The invention is also concerned with pharmaceutical compositions for use in human and veterinary therapy comprising as an essential active ingredient at least one compound represented by formula I or a pharmaceutically acceptable acid addition salt thereof in association with a pharmaceutical carrier or excipient therefor.

Another object of the present invention is concerned with a process for preparing pharmaceutical compositions for use in human or veterinary therapy comprising the association of at least one compound represented by formula I or a pharmaceutically acceptable acid addition salt thereof with a pharmaceutical carrier or excipient therefor.

As will be further demonstrated in detail, the compounds of formula I have been found to possess valuable phamacological activity, in particular antidepressive and antiaggressive properties.

Hence, a further object of the invention is to provide a method for treating pathological states of depression or aggressivity in a human or animal host in need of such treatment, comprising the administration to said host of at least one compound of formula I or a pharmaceutically acceptable acid addition salt thereof.

The compounds of formula I may be prepared by reacting, in an appropriate medium such as ethanol and in the presence of an alkali metal alcoholate, for example sodium methylate or ethylate, a nitrile of the general formula:

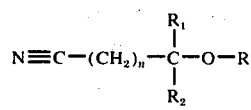    II wherein R, $R_1$, $R_2$ and $n$ have the same meanings as in formula I, with hydroxylamine hydrochloride to obtain the desired compound of formula I in free base form which may be further treated with an organic or inorganic acid to form the corresponding pharmaceutically acceptable acid addition salt thereof.

The nitriles of formula II may be obtained by various processes, according to the nitrile desired from a common starting-product which is a phenolic compound corresponding to the general formula:

HO—R    III wherein R has the same meaning as in formula I.

All the compounds of formula III are known compounds.

When $n$ is 0, the compounds of formula II may be prepared as follows:

a. A compound of formula III is heated in an appropriate medium and in the presence of a base such as anhydrous potassium carbonate or sodium hydride with an α-halogenated aliphatic ester of the general formula:

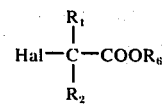    IV wherein $R_1$ and $R_2$ have the same meanings as in formula I, Hal represents a chlorine or bromine atom and $R_6$ represents a lower alkyl radical such as methyl or ethyl and the resulting alkyl oxyalkanoate derivative is converted to the corresponding amide by reaction with ammonia in gaseous form or in an aqueous concentrated solution.

The amidification can be effected in a hydroalcoholic medium or in a pure alcoholic medium such as pure methanol or ethanol or again in methanol containing a small quantity of sodium methylate.

The amide so obtained is then treated with a dehydrating agent, for example phosphorus pentoxide in a solvent such as toluene or with phosphorus oxychloride or thionyl chloride in a solvent such as benzene to obtain the required compound of formula II.

All the compounds of formula IV are known compounds. Or b. A compound of formula III is condensed with a compound of the general formula:

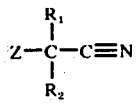     V wherein $R_1$ and $R_2$ have the same meanings as in formula I and Z represents a chlorine or bromine atom or a benzenesulphonoxy or p-toluenesulphonoxy group. The reaction may be effected in an appropriate medium such as for example methyl ethyl ketone or dimethylformamide and in the presence of sodium hydride or an alkali metal carbonate such as sodium carbonate to obtain the required compound of formula II.

All the compounds of formula V are known compounds.

When $n$ is 1 or 2, the compounds of formula II may be obtained by condensing a compound of formula III with a halogenonitrile of the general formula:

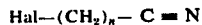     VI wherein $n$ represents the values 2 or 3 and Hal represents a halogen atom such as a chlorine or bromine atom. The reaction is undertaken in the presence of sodium hydride in a solvent such as dimethylformamide.

Following a variation of procedure, the compounds of formula II wherein $n$ is 1 can be obtained by reacting a compound of formula III in an excess of acrylonitrile in the presence of a catalyst such as for example cupric acetate or trimethylbenzylammonium hydroxide.

As mentioned above the amidoxime derivatives of formula I have been found to possess valuable pharmacological properties which are likely to render them useful in human and veterinary therapy.

In particular, the compounds of the invention have been found to present psychotropic properties and more particularly thymoanaleptic properties producing very marked antidepressive and antiaggressive effects. In the case of certain compounds of the invention the antidepressive properties are predominant and are similar to those of tricyclic antidepressants. However, at antidepressive doses, there are none of the sedative effects characteristic of the latter.

As an example of a tricyclic antidepressant, particular mention may be made of imipramine i.e. 5-(3-dimethylaminopropyl)-10,11-dihydro-5H-dibenz [b,f] azepine, which is at present one of the most widely used antidepressants.

In the remaining compounds of the invention, on the other hand, it is the antiaggressive factor which predominates.

Trials have shown that the compounds of the invention do not exert any effect on peripheral noradrenergic processes, whereas they do influence central noradrenergic processes. As against this, all the antidepressants used in clinical practice, such as imipramine for example, potentiate all the peripheral effects of exogenous norepinephrine from 1mg/kg upwards by intravenous route which results in disorders of the heart and arterial pressure. It is, in fact, known that imipramine, for example, exerts at low doses sympathomimetic effects which can provoke arterial hypertension. On the other hand, at high doses, imipramine acts more as a sympatholytic or adrenolytic agent thus producing orthostatic hypotension.

A patient treated with imipramine or a related substance must consequently be kept under constant supervision which means that such treatment can only be carried out when the patient is hospitalized.

The compounds of the invention, on the other hand, have not shown any adrenolytic or ganglioplegic properties and therefore do not exert any influence on arterial pressure regardless of the doses employed.

Furthermore, the fact that the compounds of the invention do not exert any effect on the peripheral noradrenergic processes means that they present an undeniable advantage over imipramine as they will not provoke any undesirable side-effects on the cardiac system such as arrhythmia or tachycardia as imipramine may do.

It has also been possible to demonstrate that unlike the tricyclic antidepressants of the imipramine type, there are no contraindications on the cardiac plane when the compounds of the invention are associated with inhibitors of monoamine oxydase (IMAO).

It is, in fact, well known that the association of IMAO with tricyclic antidepressants is strictly contraindicated by reason of the tropism of the IMAO with respect to the cardiac system.

The originality of those compounds of the invention in which the antiaggressive activity predominates lies in the fact that the antiaggressive action becomes apparent at very low doses in the region of 0.1mg/kg so that the antiaggressive action becomes practically specific in these compounds. Similarly, these compounds potentiate barbital at a dose as low as 1mg/kg by oral route which indicates the presence of powerful psychotropic properties.

Furthermore, these latter compounds exert their effect at doses which do not influence behaviour which means that there need be no fear of neuromuscular lesions.

At present, only the thymoanaleptics of the imipramine type exert an antiaggressive effect in pharmacology. However, at doses devoid of any influence on behaviour, this antiaggressive effect is much less specific than that observed with the typically antiaggressive compounds of formula I.

Similarly, compounds are already known which are specific inhibitors of aggressivity in the animal but none of them has been adopted for general use by the Medical Profession in human or veterinary therapy. It is known, for example, from Arch. Int. Pharmac. 186, 287–297 (1970) that two derivatives of dimethoxytriazoloisoquinoline possess specific inhibitory properties against aggressivity in the animal at doses devoid of any effect on behaviour. However, these derivatives possess strong emetic properties which render them difficult to use for therapeutic purposes.

The specifically antiaggressive compounds of the invention, on the other hand, do not present these undesirable side-effects.

In accordance with present knowledge, the method which is generally used to combat aggressivity consists in administering neuroleptics to the subject under treatment. However, the use of these neuroleptics is very often accompanied by undesirable side-effects of the extrapyramidal type such as rigidity, catalepsy and tremors which it is necessary to prevent with antidepressants.

The specifically antiaggressive compounds of the invention are characterized by the absence of extrapyramidal effects and eliminate the need for the frequently used association of a neuroleptic and an antidepressant to combat aggressivity.

Furthermore, the neuroleptics are generally adrenolytics of the α-receptor-blocking type which consequently provoke vaso-dilation and orthostatic hypotension. These undesirable side-effects can thus be avoided as the specifically antiaggressive compounds of formula I are not adrenolytic.

These pharmacological properties taken as a whole are likely to render the compounds of the invention useful in treating depressive states of all kinds requiring either a thymoanaleptic action with a view to improving the patients outlook as in cases of melancholia or a specifically antiaggressive action, for example in oligophrenia.

In veterinary therapy the specifically antiaggressive compounds of the invention can be used in place of neuroleptics with a view to preventing the aggressivity developed by certain animals when being transported, such as in the case of cattle.

Like pain, the various types of depression are numerous and constitute one of the most widespread disorders. For this reason, it is very difficult for the doctor to choose amongst the various antidepressant drugs at his disposal, that which will be effective for the case under treatment. When faced with a case of depression, the psychiatrist is often obliged to feel his way by trying several antidepressant drugs one after the other until he discovers the most suitable medication.

For this point of view, the compounds of the invention will constitute valuable additions to the therapeutic arsenal at the disposal of the doctor and, if necessary, will provide useful replacement medication for a drug which has become ineffective for any reason such as, for example, a change in the state of the patient or habituation.

Similarly, the specifically antiaggressive compounds of the invention will constitute a marked progress in psychiatric therapy when it is desired to combat pathological aggressivity. As stated above there is at present no specific drug at the disposal of the Medical Profession for combating such states.

The compounds of the invention which have been found to be particularly useful as pure thymoanaleptics of the imipramine type are:

2-(7-Benzofuryloxy)-propionamidoxime
2-(4-Benzofuryloxy)-propionamidoxime
2-(2,3-Dihydro-7-benzofuryloxy)-propionamidoxime and
3-(7-Benzofuryloxy)-propionamidoxime.

As specific antiaggressive agents the following compounds may be cited:

2-(1-Naphthyloxy)-propionamidoxime
2-(1-Naphthyloxy)-butyramidoxime and
3-(2-Naphthyloxy)-propionamidoxime.

Pharmacological trials have been undertaken with a view to determining the presence of the various properties which, taken together, are capable of rendering the compounds of the invention useful as antidepressant or antiaggressive agents.

Preferably, the compounds of the invention were studied in the form of a pharmaceutically acceptable acid addition salt such as the hydrochloride or the oxalate.

As it is not possible to find or to create a drepressive state in the animal, the compounds of the invention were studied in accordance with classical procedures namely by verifying whether they present in the animal the same properties as the known antidepressants recognized as being active in human therapy.

It is, therefore, very difficult to estimate the effectiveness of a compound on the basis of a single test. A compound which shows only relatively slight activity in a particular test should not be automatically considered to be ineffective.

Only the overall results of several tests make it possible to form a good opinion as regards the action of a compound as being a potentially antidepressive agent.

1. Determination of thymoanaleptic properties

The thymoanaleptic properties of the compounds of the invention were determined by means of reserpine-induced ptosis and hypothermia in the rat.

a. Reserpine-induced ptosis

The antidepressants antagonize or delay the sedative action of reserpine as measured by means of, for example, ptosis in the rat.

An intraperitoneal dose of 5 mg/kg of reserpine was administered to batches of 5 male rats of the $CF_1$ strain weighing an average of 300 g.

Thirty minutes later a dose of the compound to be studied was given by oral route and the inhibitory effect of the reserpine was noted every hour up to the sixth hour. Ptosis was evaluated for each eye in accordance with the following scale:

0 : eyelids open
1 : eyelids ¼ closed
2 : eyelids ½ closed
3 : eyelids ¾ closed
4 : eyelids completely closed.

Thus, for example, if an animal had a ptosis of 1 for one eye and 2 for the other, it was given the score of 1.5. The average of the results registered for each hour to the sixth hour was calculated for the treated animals and for the controls which had only received reserpine. The difference between these two averages represents the average decrease of the ptosis in the treated animals as compared to the controls.

The following compounds were studied in accordance with the procedure described above:

2-(1-Naphthyloxy)-propionamidoxime (Compound 1)
2-(7-Benzofuryloxy)-propionamidoxime (Compound 2)
2-(4-Benzofuryloxy)-propionamidoxime (Compound 3)
2-(2,3-Dimethyl-6-benzofuryloxy)-2-methyl-propionamidoxime (Compound 4)
2-(5-Benzofuryloxy)-acetamidoxime (Compound 5)
3-(1-Naphthyloxy)-propionamidoxime (Compound 6)
2-(7-Benzofuryloxy)-acetamidoxime (Compound 7)
3-(7-Benzofuryloxy)-propionamidoxime (Compound 8)

2-(2,3-Dihydro-7-benzofuryloxy)-propionamidoxime (Compound 9)
2-(2-Ethyl-3-benzofuryloxy)-butyramidoxime (Compound 10)
2-(1-Naphtyloxy)-2-methyl-propionamidoxime (Compound 11)
2-(2-Methyl-3-benzofuryloxy)-acetamidoxime (Compound 12)
3-(2-Ethyl-3-benzofuryloxy)-propionamidoxime (Compound 13)
2-[(1,4-Benzodioxanyl)-5-oxy]-butyramidoxime (Compound 14)
2-(2,3-Dimethyl-5-benzofuryloxy)-acetamidoxime (Compound 15)
2-(2-Methyl-3-benzofuryloxy)-propionamidoxime (Compound 16)
2-(2-Ethyl-3-benzofuryloxy)-propionamidoxime (Compound 17)
3-(2-Naphthyloxy)-propionamidoxime (Compound 18)
3-(2-Methyl-3-benzofuryloxy)-propionamidoxime (Compound 19)
2(2-Isopropyl-3-benzofuryloxy)-butyramidoxime (Compound 20)
2-(2,3-Dimethyl-6-benzofuryloxy)-acetamidoxime (Compound 21)
2-(2-Methyl-3-benzofuryloxy)-2-methyl-propionamidoxime (Compound 22)
3-(2,3-Dimethyl-5-benzofuryloxy)-propionamidoxime (Compound 23)
2-(2-Isopropyl-3-benzofuryloxy)-propionamidoxime (Compound 24)
2-(6-Benzofuryloxy)-acetamidoxime (Compound 25)
2-(4-Benzothienyloxy)-acetamidoxime (Compound 26)
2-(2-Ethyl-3-benzofuryloxy)-acetamidoxime (Compound 27)
2-(6-Benzofuryloxy)-propionamidoxime (Compound 28)
2-(5-Benzofuryloxy)-propionamidoxime (Compound 29)
2-(7-Benzofuryloxy)-2-methyl-propionamidoxime (Compound 30)
2-(6-Benzofuryloxy)-butyramidoxime (Compound 31)
3-(2-Methyl-5-benzofuryloxy)-propionamidoxime (Compound 32)
2-(2-Methyl-5-benzofuryloxy)-acetamidoxime (Compound 33)

The results obtained with the above compounds are listed in Table I which follows:

Table I

| Compound | Dose administered (in mg/kg) | Average decrease of Ptosis |
|---|---|---|
| 1 | 10 | 1.7 |
| 2 | 10 | 2.4 |
| 3 | 10 | 2.1 |
| 4 | 10 | 2.1 |
| 5 | 10 | 1.9 |
| 6 | 10 | 1.5 |
| 7 | 10 | 1.4 |
| 8 | 10 | 1.3 |
| 9 | 10 | 1.3 |
| 10 | 10 | 0.8 |
| 11 | 10 | 0.7 |
| 12 | 10 | 0.7 |
| 13 | 10 | 0.7 |
| 14 | 10 | 0.6 |
| 15 | 10 | 0.5 |
| 16 | 10 | 0.5 |
| 17 | 10 | 0.4 |
| 18 | 10 | 0.4 |

Table I-continued

| Compound | Dose administered (in mg/kg) | Average decrease of Ptosis |
|---|---|---|
| 19 | 10 | 0.3 |
| 20 | 10 | 0.3 |
| 21 | 10 | 0.3 |
| 22 | 10 | 0.3 |
| 23 | 10 | 0.2 |
| 24 | 10 | 0.2 |
| 25 | 10 | 0.2 |
| 26 | 20 | 1.4 |
| 27 | 20 | 0.3 |
| 28 | 100 | 2.4 |
| 29 | 100 | 2.4 |
| 30 | 100 | 2.3 |
| 31 | 100 | 2.3 |
| 32 | 100 | 2.3 |
| 33 | 100 | 2.0 |

A comparative test carried out with 20 mg/kg of imipramine in the same conditions gave an average decrease of ptosis of 1.6 in comparison with the controls.

b. Reserpine-induced hypothermia

The thymoanaleptics antagonize the hypothermia-inducing action of reserpine.

An intraperitoneal dose of 5 mg/kg of reserpine was administered to batches of 5 male rats $CF_1$ weighing an average of 300 g. Thirty minutes later, the rectal temperature was determined and then a dose of the compound to be tested was given by oral route, except to the control animals. The rectal temperature of all the animals including the controls was taken every hour up to the 6th hour.

The average of the results registered with the treated animals and with the controls was calculated. The difference between these two averages enabled an estimation to be made regarding the antagonistic effect of the compounds of the invention on the hypothermia induced by reserpine.

Thus, an average result of +1° C means that the compound under study produced an average increase of 1° C in the temperature previously lowered by the reserpine as compared with the controls.

The following Table II illustrates the results obtained with some of the above compounds as well as with the following compounds:

2-(1-Naphthyloxy))-butyramidoxime (Compound 34)
2-(2-Isopropyl-3-benzofuryloxy)-2-methyl-propionamidoxime (Compound 35)
2-(2-Isopropyl-3-benzofuryloxy)-acetamidoxime (Compound 36)
2-(2-Naphthyloxy)-butyramidoxime (Compound 37)
2-[(1,4-Benzodioxanyl)-5-oxyl]-2-methyl-propionamidoxime (Compound 38)
2-(2-Methyl-3-benzofuryloxy)-butyramidoxime (Compound 39)
2-(2-Naphthyloxy)-2-methyl-propionamidoxime (Compound 40)
2-(2,3-Dimethyl-7-benzofuryloxy)-butyramidoxime (Compound 41)

Table II

| Compound | Dose administered (in mg/kg) | Average inhibition of hypothermia (positive °C) |
|---|---|---|
| 1 | 10 | 0.7 |
| 2 | 100 | 0.8 |
| 3 | 20 | 1 |
| 4 | 10 | 0.6 |
| 5 | 10 | 0.5 |

Table II-continued

| Compound | Dose administered (in mg/kg) | Average inhibition of hypothermia (positive °C) |
|---|---|---|
| 7 | 10 | 0.6 |
| 8 | 10 | 0.4 |
| 9 | 10 | 0.5 |
| 11 | 20 | 0.5 |
| 14 | 10 | 0.4 |
| 20 | 10 | 0.8 |
| 22 | 10 | 0.5 |
| 23 | 10 | 0.3 |
| 24 | 10 | 0.8 |
| 28 | 100 | 1.1 |
| 29 | 100 | 0.8 |
| 30 | 100 | 1 |
| 34 | 10 | 1.1 |
| 35 | 10 | 0.7 |
| 36 | 10 | 0.7 |
| 37 | 10 | 0.5 |
| 38 | 10 | 0.5 |
| 39 | 10 | 0.3 |
| 40 | 10 | 0.2 |
| 41 | 100 | 1.1 |

A comparative trial undertaken with 10 mg/kg of imipramine, in the same conditions, gave an average inhibition of hypothermia of + 0.4 ° C.

The antidepressant activity of the compounds of the invention was confirmed by verifying whether they potentiate the toxicity of yohimbine as well as the stereotypies induced by amphetamine.

Yohimbine provokes central adrenergic effects while amphetamine causes central dopaminergic effects.

c. Potentiation of the toxicity of yohimbine

Yohimbine is a substance which provokes an increase in the serotonine level in the brain or a decrease in norepinephrine according to the author.

For this purpose, the test of QUINTON was used which is described in Brit. J. Pharmacol. 21, 51 (1963). This test was performed on male mice which received an oral dose of 50 mg/kg of the compound to be tested. Thirty minutes later, the animals were given an intraperitoneal dose of 25 mg/kg of yohimbine hydrochloride. The percentage of mortality was noted after 24 hours.

Table III hereunder expresses the percentage of potentiation of the toxicity due to yohimbine in comparison with the controls.

The percentage in question was determined 24 hours after the administration of yohimbine.

The following results were recorded with certain of the compounds hereabove cited as well as with the following compounds:
2-(7-Benzofuryloxy)-butyramidoxime (Compound 42)
2-(4-Benzofuryloxy)-butyramidoxime (Compound 43)
2-(2,3-Dimethyl-7-benzofuryloxy)-propionamidoxime (Compound 44)
2-[(1,4-Benzodioxanyl)-5-oxy]-propionamidoxime (Compound 45)
2-(2-Ethyl-3-benzofuryloxy)-2-methyl-propionamidoxime (Compound 46)

Table III

| Compound | Potentiation of the toxicity of Yohimbine (in %) |
|---|---|
| 2 | 50 |
| 3 | 40 |
| 4 | 30 |
| 5 | 10 |
| 6 | 30 |
| 7 | 60 |
| 8 | 30 |
| 9 | 10 |
| 10 | 10 |
| 15 | 10 |
| 17 | 20 |
| 18 | 10 |
| 19 | 10 |
| 21 | 40 |
| 24 | 30 |
| 25 | 30 |
| 27 | 20 |
| 34 | 10 |
| 38 | 10 |
| 39 | 40 |
| 42 | 60 |
| 43 | 60 |
| 44 | 40 |
| 45 | 10 |
| 46 | 10 |

At the dose of 20 mg/kg, under the same conditions, Compound 1 potentiates by 50 % the toxicity of yohimbine.

In this test, imipramine at a dose of 50 mg/kg produced a 50 %-potentiation of the toxicity induced by yohimbine.

Other trials undertaken with 20 mg/kg of Compound 26, by oral route, produced a 50 %-potentiation of the toxicity of 10 mg/kg of yohimbine 24 hours after injection of the latter.

d. Potentiation of the stereotypies induced by amphetamine

It is commonly admitted that amphetamine induces stereotypies by stimulating the dopaminergic receptors and inhibiting the re-uptake of dopamine into the neuron.

The thymoanaleptics potentiate these stereotypies.

An intraperitoneal dose of 10 mg/kg of amphetamine was administered to batches of 5 rats maintained in individual cages. Thirty minutes later, a dose of 10 mg/kg of the compound to be tested was given by oral route. Note was taken of the intensity of the stereotypies every 30 minutes for 150 minutes in accordance with the following scale which indicates the behaviour of the animal.

0 : the rat is motionless and asleep
1 : the rat is motionless and awake
2 : the rat is mobile but does not present stereotyped (repeated) movements
3 : the rat stands on its hind paws and sniffs the lid of its cage in a stereotyped manner.
4 : the rat licks the walls of its cage in a stereotyped manner
5 : the rat bites the bars of its cage or sniffs the shavings of its litter in a stereotyped manner
6 : the rat chews the shavings in a stereotyped manner The average of the 5 results obtained for each batch was calculated and compared with the average obtained with the control animals.

The difference between these averages represents the mean increase of the stereotypies of the treated animals in comparison with the controls.

The results obtained with the above compounds are listed in Table IV hereunder.

Table IV

| Compound | Average increase of the stereotypies |
|---|---|
| 1 | 1 |
| 2 | 9 |

Table IV-continued

| Compound | Average increase of the stereotypies |
|---|---|
| 3 | 8.6 |
| 4 | 0.8 |
| 7 | 4.8 |
| 8 | 5.6 |
| 9 | 6.2 |
| 10 | 5.6 |
| 13 | 2.4 |
| 14 | 4.2 |
| 15 | 1 |
| 17 | 1.2 |
| 21 | 4.2 |
| 22 | 4.2 |
| 24 | 3.8 |
| 25 | 4.4 |
| 35 | 3 |
| 36 | 1.8 |
| 37 | 1.8 |
| 43 | 5.5 |
| 45 | 3 |
| 46 | 6.6 |

At a dose of 20 mg/kg, under the same conditions, Compounds 29, 30 and 33 gave average increases of stereotypies of 5, 6.5 and 4 respectively.

A comparative trial carried out with 20 mg/kg of imipramine under the same conditions gave an average increase of stereotypies of 6.

Other trials performed with 20 mg/kg of Compound 26, by oral route and in the same conditions, gave means increases of 6.8 of the stereotypies provoked by 5 mg/kg of amphetamine.

It was also demonstrated that, at a dose of 0.05 mg/kg by intragastric route, Compound 2 potentiates the stereotypies induced by amphetamine to a more marked degree for 150 minutes than 5 mg/kg of imipramine under the same conditions. The average increase of the stereotypies for Compound 2 is 9 and for imipramine 4.4.

2. Determination of antiaggressive properties

The antiaggressive properties of the compounds of the invention were determined by means of the killer rats and isolated mice aggressivity tests.

a. Aggressivity of killer rats

If, under certain conditions, male rats are kept alone in individual cages for several weeks, the become spontaneously aggressive towards any mouse, which they kill as soon as it is placed in the same cage.

Mice were introduced one after another into cages containing an isolated rat and a selection was made of the rats which immediately killed three mice. In this way batches of 6 to 8 rats were constituted. The rats were then given the compound to be studied by intraperitoneal route in such a way that each batch received a higher dose than the preceding batch. At different times after administration, three mice were successively introduced into the cage and the percentage of reduction in aggressivity was calculated at a selected time after administration and on the basis of the dose given.

Table V which follows contains the results obtained 30 minutes after administration of the compound to be studied.

Table V

| Compound | Dose administered (in mg/kg) | % of inhibition of aggressivity |
|---|---|---|
| 1 | 3 | 100 |
| 2 | 20 | 50 |
| 3 | 20 | 89 |
| 4 | 25 | 25 |
| 5 | 25 | 60 |
| 6 | 25 | 30 |
| 8 | 25 | 70 |
| 12 | 25 | 27 |
| 14 | 25 | 80 |
| 18 | 25 | 100 |
| 26 | 25 | 27 |
| 30 | 20 | 75 |
| 33 | 20 | 60 |
| 34 | 1 | 100 |
| 46 | 25 | 100 |

A comparative test undertaken with 20 mg/kg of imipramine under the same conditions showed a 45 %-inhibition of aggressivity.

The above Table shows more particularly that Compounds 1, 18 and 34 possess powerful antiaggressive properties.

b. Aggressivity of isolated mice

If a male mouse is kept alone in a cage for 3 weeks to 1 month, it will spontanesouly attack any other animal of the same species which is placed in the same cage. If the other animal has also been isolated under the same conditions a series of fights takes place.

Mice were isolated for the period of time required to render them spontaneously aggressive. Couples were then put together and note was taken of the number of fights which took place over a period of 3 minutes. Each batch was composed of four pairs of mice.

The animals of each batch were then treated by intragastric route with the compound to be studied which was administered in such a way that each batch received a higher dose than the preceding batch. Thirty minutes after administration, the couples were placed together again for a further three minutes and the number of fights noted.

The results were expressed in the percentage of decrease in the number of fights between the animals after treatment in comparison with the percentage obtained before treatment which represents the percentage of inhibition of aggressivity.

Trials undertaken by oral route showed that Compound 1 at a dose of 0.63 mg/kg provokes a 50 %-inhibition of aggressivity ($=ED_{50}$).

A comparative trial revealed that 20 mg/kg of imipramine provokes an inhibition of 78 %. A test performed with Compound 1 by intragastric route showed that 0.42 mg/kg of this compound inhibited aggressivity by 50 % ($ED_{50}$) 90 minutes after administration. The same activity was obtained with a dose of imipramine which was twenty-times greater.

3. Determination of cholinolytic properties

Action with respect to tremorine

When injected into mice, tremorine and its metabolite, oxotremorine, produce central cholinergic effects, i.e. normal and provoked tremor as well as peripheral cholinergic effects i.e. weeping, seating diarrhea and salivation.

The purpose of this series of tests was to demonstrate that the compounds of the invention are devoid of cholinolytic activity which gives rise to undesirable side-effects such as dryness of the mouth, difficulties in optical accommodation and tachycardia.

Male mice of the $OF_1$ strain weighing 22 g, were divided into batches of 10. Each batch with the exception of the control animals, received, by oral route, a dose of the compound to be tested.

Thirty minutes later, 10 mg/kg of tremorine were administered to all the batches and thirty minutes after the injection of tremorine note was taken of the cholinergic effects on each animal in accordance with the following scale:

0 : no action
1 : slight action
2 : average action
3 : strong action
4 : very strong action The difference between the results obtained with the controls and the treated animals represents the decrease of the cholinergic effects provoked by tremorine. No decrease means that the compound under study does not possess cholinolytic properties.

The differences in question are listed in the following Table VI, these differences being obtained with the compounds of the invention in comparison with imipramine.

Table VI

| Compound | Peripheral cholinergic response | | | Central response tremor | |
|---|---|---|---|---|---|
| | Weeping | Sweating | Salivat. | Normal | Provoked |
| 1 (5 mg/kg) | 0 | 0 | 0 | 0 | 0 |
| 13 (25 mg/kg) | 0 | 0 | 0 | 0 | 0 |
| 17 (25 mg/kg) | 0 | 0 | 0 | −0.8 | 0 |
| 22 (10 mg/kg) | 0 | 0 | 0 | 0 | 0 |
| Imipramine (20 mg/kg) | −0.8 | −2 | 0 | −4 | −0.4 |

These results show that the compounds of the invention do not antagonize the peripheral effects provoked by tremorine and are almost without action on the central effects due to tremorine.

Tests were also performed with a view to determining whether the compounds of the invention modify spontaneous motricity. Compounds 2, 3, 8 and 9 were found to have no influence on the spontaneous motricity in the mouse when administered at the dose of 50 mg/kg by intragastric route.

Similarly, it was demonstrated that 3 mg/kg of Compound 1, by intragastric route, reduced spontaneous motricity also in the mouse by 50 % 30 minutes after administration without, however modifying the curiosity of the animal.

However, the doses of Compound 1 which are active on aggressivity are far removed from those which decrease motricity as shown by the ratio:

$$\frac{ED_{50} \text{ (recorded in the motricity test)}}{ED_{50} \text{ (recorded in the test on isolated mice)}}$$

namely $\frac{3}{0.63} \simeq 5$.

This figure proves that Compound 1 is not sedative at the doses which are active against aggressivity.

It was also demonstrated that in the rat and the mouse, the active doses which were capable of inhibiting aggressivity completely or partially did not affect the behaviour of the animal.

For example, in the case of Compound 1, the neurotoxic dose 50 (NTD 50) which was determined by means of the rotarod test of BOISSIER (Therapie 1958, XIII, pp 1074–1118) 30 minutes after oral administration to the mouse was sufficiently far removed from the $ED_{50}$ determined in the aggressivity test on the isolated mouse to avoid any damage to the neuromuscular functions.

This conclusion can be expressed by the following ratio:

$$\frac{NTD_{50} \text{ (recorded in the rotarod test)}}{ED_{50} \text{ (recorded in the test on isolated mice)}} = \frac{6}{0.63} \simeq 10$$

With regard to Compound 2, it was found that this compound did not cause any damage to the neuromuscular functions up to 40 mg/kg by oral route for 3 hours after administration.

A pharmacological test was also carried out on the anesthetized cat with a view to demonstrating that Compound 1 is devoid of ganglioplegic activity.

The tonus of the nictitating membrane was first noted after which the contractile reaction of the membrane to electric stimulation of the preganglionic fibre of the cervical sympathetic nerve was tested.

It was found that intravenous doses of 0.005, 0.1 and 1 mg/kg did not modify the intensity of the contractions of the membrane provoked by the electric stimulation. This proves that Compound 1 is devoid of ganglioplegic effects.

Another pharmacological test undertaken on the dog anaesthetized with sodium pentobarbital and atropinized showed that intravenous doses of 0.005, 0.1 and 1 mg/kg of Compound 1 did not modify the hypertensive effect of epinephrine injected into the vein. This result proves that Compound 1 is also devoid of adrenolytic properties.

Finally, tests of toxicity were performed with compounds of the invention following the method of KARBER and BEHRENS. The following results were recorded:

a) By intraperitoneal route on mice

| Compound | $LD_{50}$ (in mg/kg) |
|---|---|
| 2 and 3 | 68 (after 48 hours) | b) By intraperitoneal route on rats

| Compound | $LD_{50}$ (in mg/kg) |
|---|---|
| 1 | 50 (after 24 hours) |
| 2 | 62.5 (after 48 hours) | c) By oral route on mice

| Compound | $LD_{50}$ (in mg/kg) |
|---|---|
| 1 | 380 (after 24 hours) |
| 2 | 170 (after 48 hours) | d) By oral route on rats

| Compound | $LD_{50}$ (in mg/kg) |
|---|---|
| 1 | 108 (after 24 hours) |
| 2 | 440 (after 48 hours) |

The other compounds of the invention showed in general a $LD_{50}$ superior to 250 mg/kg by oral route in mice.

It will be appreciated that for therapeutic use the compounds of the invention will normally be administered in the form of a pharmaceutically or veterinary composition comprising as an essential active ingredient at least one compound of formula I or a pharmaceutically acceptable acid addition salt thereof, in association with a pharmaceutical carrier or excipient therefor. The carrier may be a solid or liquid diluent or excipient of the kind normally employed in the production of medicaments ready for use, for example lactose, starches, talc, magnesium stearate, polyvinylpyrrolidone, alginic acid, colloidal silica and microcrystalline cellulose. The composition may be made up in a form suitable for the desired mode of administration which may be by the oral, rectal or parenteral route.

Advantageously for clinical use, the composition is made up in a dosage unit form adapted for the desired mode of administration. The dosage unit may be, for example a coated- or uncoated tablet, a hard or soft gelatin capsule, a suspension, a powder, or a syrup for oral administration, a suppository for rectal administratiion, or a solution for parenteral administration.

The amount of active ingredient in each dosage unit will be such that one or more units are required for each therapeutic administration.

The following Examples illustrate the preparation of the compounds of the invention as well as that of the compositions containing the said compounds:

EXAMPLE 1

Preparation of 2-(2,3-dimethyl-7-benzofuryloxy)-propionamidoxime a) Ethyl 2-(2,3-dimethyl-7-benzofuryloxy)-propionate Under vigorous stirring, a mixture of 16.2 g, (0.1 mol) of 2,3-dimethyl-7-hydroxy-benzofuran, 13.8 g (0.1 mol) of dry and finely divided potassium carbonate and 50 ml of methyl ethyl ketone was refluxed for 30 minutes. The reaction medium was allowed to cool to room temperature and a solution of 19.9 g (0.11 mol) of ethyl 2-bromo-propionate in 25 ml of methyl ethyl ketone was added drop-by-drop. Rapid stirring and heating under reflux were maintained for 22 hours.

After cooling, the inorganic salts were filtered off, the solvent was evaporated under reduced pressure and the residue so obtained was taken up in ethyl ether. The etereal solution was first washed with a 5 % solution of sodium hydroxide and then with water after which the mixture was dried on anhydrous sodium sulphate and distilled.

In this manner, 20.7 g of ethyl 2(2,3-dimethyl-7-benzofuryloxy)-propionate were prepared, boiling at 132°–135° C under 0.25 mm of Hg, which represents a yield of 79 % of the theoretical value.

$n_D^{24} = 1.5263$

By following the same procedure as that described above but using the appropriate starting-products the compounds listed hereunder were prepared:

| Compound | Boiling point °C |
|---|---|
| Ethyl 2-(2-methyl-5-benzofuryloxy)-propionate | 122–123 (0.2 mm.Hg) |
| $n_D^{25} = 1.5258$ Methyl 2-(7-benzofuryloxy)-2-methyl-propionate | 111–115 (0.3 mm.Hg) |
| M.P. 55–57°C Ethyl 2-(2,3-dimethyl-7-benzofuryloxy)-valerianate | 145–148 (0.5 mm.Hg) |
| $n_D^{24} = 1.5175$ Ethyl 2-(2,3-dimethyl-7-benzofuryloxy)-butyrate | 138–140 (0.22 mm.Hg) |
| $n_D^{27} = 1.5184$ Ethyl 2-(1-naphthyloxy)-2-methyl-propionate | 115–116 (0.3 mm.Hg) |
| $n_D^{25.5} = 1.5564$ Methyl 2-(2-naphthyloxy)-2-methyl-propionate | 118–120 (0.15 mm.Hg) |
| $n_D^{26} = 1.5693$ Methyl 2-[(1,4-benzodioxanyl)-5-oxy]-2-methyl-propionate | 120–136 (0.1 mm.Hg) |
| $n_D^{28} = 1.5225$ Ethyl 2-(2,3-dimethyl-6-benzofuryloxy)-2-methyl-propionate | 115–120 (0.4 mm.Hg) |
| $n_D^{25} = 1.5258$ Ethyl 2-(1-naphthyloxy)-valerianate | 140–142 (0.1 mm.Hg) |
| $n_D^{27} = 1.5528$ Methyl 2-(7-Benzofuryloxy)-valerinate | 127–130 (0.5 mm.Hg) |
| $n_D^{24.5} = 1.5218$ | | b) 2-(2,3-Dimethyl-7-benzofuryloxy)-propionamide

To a solution of 23.6 g (0.09 mol) of ethyl 2-(2,3-dimethyl-7-benzofuryloxy)-propionate in 100 ml of 95° ethanol, were added 100 ml of a concentrated ammonia solution. The mixture was stirred for 16 hours and then diluted with water. The reaction medium was cooled with iced water after which the precipitate was filtered off.

In this manner, 16.8 g of 2(2,3-dimethyl-7-benzofuryloxy)-propionamide were obtained, melting at 164°–165° C after recrystallization from benzene which represents a yield of 80 % of the theoretical value.

By following the same procedure as that described above but using the appropriate starting-products, the compounds listed hereunder were prepared:

| Compound | Melting point °C |
|---|---|
| 2-(2-Methyl-5-benzofuryloxy)-propionamide | 124–126 |
| 2-(2,3-Dimethyl-7-benzofuryloxy)-valeramide | 181–182 |
| 2-(2,3-Dimethyl-7-benzofuryloxy)-butyramide | 186–187 |
| 2-[(1,4-Benzodioxanyl)-5-oxy]-2-methyl-propionamide | 143–146 |
| 2-(2,3-Dimethyl-6-benzofuryloxy)-2-methyl-propionamide | 135–137 |
| 2-(7-Benzofuryloxy)-2-methyl-propionamide | 112–115 |
| 2-(1-Naphthyloxy)-valeramide | 145–147 |
| 2-(7-Benzofuryloxy)-valeramide | 146–148 |

Using the same method as that hereabove described, the following compounds were prepared taking into account the variations of process given hereunder:

2-(1Naphthyloxy)-2-methyl-propionamide by reacting, for 7 days, the appropriate starting-product with a saturated ammonia solution in methanol and in the presence of a catalytic amount of sodium methylate. The compound was used in crude form.

2-(2-Naphthyloxy)-2-methyl-propionamide by reacting the appropriate starting-product with a saturated ammonia solution in methanol. M.P. 116°–119° C.

c) 2-(2,3-Dimethyl-7-benzofuryloxy)-propionitrile

To a solution of 22.7 g (0.09 mol) of 2-(2,3-dimethyl-7-benzofuryloxy)-propionamide in 450 ml of dry toluene were added 70 g of phosphorus pentoxide. The mixture was heated under reflux for 24 hours and then allowed to cool to 50° C. The toluene was decanted out and the residue so obtained was taken up in 100 ml of fresh toluene. The solution was heated to boiling for 20 minutes, allowed to cool and decanted. These last three operations were repeated twice. The organic solutions were collected, evaporated to dryness under vacuum and the residue was distilled.

In this manner, 16.3 g of 2-(2,3-dimethyl-7-benzofuryloxy)-propionitrile were obtained, boiling at 104°–106° C under 0.35 mm. Hg, which represents a yield of 78 % of the theoretical value. M.P. 53°–55° C.

By following the same procedure as that described above but using the appropriate starting-products, the compounds listed hereunder were prepared:

| Compound | Boiling point°C |
| --- | --- |
| 2-(2-Methyl-5-benzofuryloxy)-propionitrile | 100–104 (0.3 mm. Hg) |
| $n_D^{27} = 1.5457$ | |
| 2-(2,3-Dimethyl-7-benzofuryloxy)-butyronitrile | 132–134 (0.35 mm. Hg) |
| $n_D^{28} = 1.5306$ | |
| 2-(2,3-Dimethyl-7-benzofuryloxy)-valeronitrile | used in crude form |
| 2-(7-Benzofuryloxy)-2-methyl-propionitrile | 95–97 (0.15 mm. Hg) |
| $n_D^{28} = 1.5304$ | |
| 2-[(1,4-Benzodioxanyl)-5-oxy]-2-methyl-propionitrile | 129–132 (0.02 mm. Hg) |
| $n_D^{24} = 1.5232$ | | d) 2-(2,3-Dimethyl-7-benzofuryloxy)-propionamidoxime

To a mixture containing 10.75 g (0.05 mol) of 2-(2,3-dimethyl-7-benzofuryloxy)-propionitrile and 3.47 g (0.05 mol) of hydroxylamine hydrochloride in 75 ml of ethanol, was added drop-by-drop and under stirring, a solution of sodium ethylate obtained from 1.15 g (0.05 at.g) of sodium in 35 ml of ethanol.

The reaction medium was refluxed for 3 hours and allowed to stand for 16 hours at 20° C after which it was filtered and evaporated to dryness under reduced pressure. The residue so obtained was taken up in ether and the ethereal phase was washed with water, dried over anhydrous sodium sulphate and evaporated to dryness under reduced pressure. The solid residue so obtained was then purified by crystallisation from a n-hexane/isopropanol mixture.

In this manner, 2-(2,3-dimethyl-7-benzofuryloxy)-propionamidoxime was obtained in free base form melting at 136°–138° C. Yield: 76 % of the theoretical value.

The free base so obtained was converted to its hydrochloride, oxalate, hydrobromide and methanesulphonate in the following manner.

Hydrochloride

The 2-(2,3-dimethyl-7-benzofuryloxy)-propionamidoxime base obtained was taken up in ether and a hydrochloric acid solution in ether was added. The hydrochloride so formed was then recrystallised from an isopropanol/isopropyl ether mixture.

In this manner, 5.84 g of 2-(2,3-dimethyl-7-benzofuryloxy)propionamidoxime hydrochloride was obtained which represents a yield of 41 % of the theoretical value.

M.P. 191°–194° C after recrystallisation from pure isopropanol.

Neutral oxalate

To a solution of 2-(2,3-dimethyl-7-benzofuryloxy)-propionamidoxime base in ether, was added under stirring and until an acid reaction was obtained, an oxalic acid solution in ether.

The oxalate which precipitated was centrifuged out and purified by crystallisation from a methyl ethyl ketone/ether mixture.

In this manner, 2-(2,3-dimethyl-7-benzofuryloxy)-propionamidoxime neutral oxalate was obtained melting at 147°–148° C with decomposition.

Hydrobromide

To a solution of 2-(2,3-dimethyl-7-benzofuryloxy)-propionamidoxime base in methanol, was added while stirring concentrated hydrobromic acid until an acid reaction was obtained.

The solution was evaporated to dryness under reduced pressure and the semisolid residue was taken up in ether where it crystallised. The hydrobromide so obtained was purified by crystallisation in a methyl ethyl ketone/ether mixture.

In this manner, 2-(2,3-dimethyl-7-benzofuryloxy)-propionamidoxime hydrobromide was obtained, melting at 168°–171° C with decomposition.

Methanesulphonate 2-(2,3-Dimethyl-7-benzofuryloxy)-propionamidoxime methanesulphonate was obtained following the same procedure as for the hydrobromide but replacing hydrobromic acid with methanesulphonic acid.

M.P. of the methanesulphonate: 129°–132° C.

Using the same method as that described hereabove but using the appropriate starting-products, the following compounds were prepared:

| Compound | Melting point °C |
| --- | --- |
| 2-(2,3-Dimethyl-7-benzofuryloxy)-butyramidoxime hydrochloride | 189–193 |
| 2-(7-Benzofuryloxy)-2-methyl-propionamidoxime hydrochloride | 162–164 |
| 2-(2,3-Dimethyl-7-benzofuryloxy)-valeramidoxime hydrochloride | 193–197 |
| 2-[(1,4-Benzodioxanyl)-5-oxy]-2-methyl-propionamidoxime hydrochloride | 173–175 |
| 2-(2-Methyl-5-benzofuryloxy)-propionamidoxime hydrochloride | 174–177 |

EXAMPLE 2

Preparation of 2-(7-benzofuryloxy)-butyramidoxime hydrochloride a) 2-(7-Benzofuryloxy)-butyronitrile To a solution of 67 g (0.5 mol) of 7-hydroxy-benzofuran in 250 ml of dimethylformamide were added 75.9 g (0.55 mol) of finely ground anhydrous potassium carbonate. While stirring the reaction mixture was heated for 1 hour to about 70°–80° C, cooled and, while still stirring, 123.75 g (0.55 mol) of 2-benzenesulphonyloxy-butyronitrile were added. Stirring was maintained for 15 hours, after which the reaction medium was heated for 1 hour at 70°–80° C, cooled and filtered. The solvent was evaporated out under reduced pressure and the residue obtained was taken up in ether. The organic solution was washed first with water, then with a 5 % solution of sodium hydroxide and finally with water. The mixture was dried over anhydrous sodium sulphate, the solvent was evaporated out and the residue was fractionated by distillation.

In this manner 89 g of 2-(7-benzofuryloxy)-butyronitrile were obtained, boiling at 115°–120° C under 0.6 mm. Hg, which represents a yeild of 89 % of the theoretical value.

$n_D^{24} = 1.5355$

By following the same procedure as that described above but using the appropriate starting-products, the compounds listed hereunder were prepared:

| Compound | Boiling point °C |
| --- | --- |
| 2-(5-Benzofuryloxy)-propionitrile | 103–105 (0.3 mm.Hg) |
| $n_D^{30} = 1.5450$ | |
| 2-(6-Benzofuryloxy)-propionitrile hydrochloride | 130–132 (0.45 mm.Hg) 164– |
| $n_D^{24} = 1.5497$ | |
| 2-(4-Benzofuryloxy)-butyronitrile | 96–97 (0.3 mm.Hg) |
| $n_D^{26} = 1.5362$ | |
| 2-(2,3-Dimethyl-6-benzofuryloxy)-butyrami- | |
| 2-(5-Benzofuryloxy)-butyronitrile | 145–(1,4-Benzodioxanyl)-5:oxy]- (0.5 mm.Hg) |
| $n_D^{26} = 1.5360$ | |
| 2-(6-Benzofuryloxy)-butyronitrile | 122–124 (0.55 mm.Hg) |
| $n_D^{25} = 1.5370$ | |
| 2-(2,3-Dimethyl-5-benzofuryloxy)-2-propionitrile | 120–125 (0.4 mm.Hg) |
| $n_D^{30} = 1.5523$ | |
| 2-(2,3-Dimethyl-5-benzofuryloxy)-butyronitrile | 121–124 (0.35 mm.Hg) |
| $n_D^{26} = 1.5308$ | |
| 2-(2,3-Dimethyl-6-benzofuryloxy)-butyronitrile | 112–116 (0.2 mm.Hg) |
| $n_D^{29} = 1.5321$ | |
| 2-[(1,4-Benzodioxanyl)-5-oxy]-butyronitrile | 130–138 (0.32 mm.Hg) |
| $n_D^{26} = 1.5284$ | |
| 2-(1-Naphthyloxy)-butyronitrile | 108–114 (0.08 mm.Hg) |
| $n_D^{25} = 1.5780$ | |
| 2-(2-Naphthyloxy)-butyronitrile | 120–130 (0.25 mm.Hg) |
| $n_D^{24} = 1.5771$ | |
| 2-(2,3-Dimethyl-6-benzofuryloxy)-propionitrile | 102–103 (0.2 mm.Hg) |
| $n_D^{26} = 1.5419$ | | b) 2-(7-Benzofuryloxy)-butyramidoxime hydrochloride

This compound was obtained in accordance with the method described in Example 1 (d) starting from 2-(7-benzofuryloxy)-butyronitrile.

M.P. 129°–130° C after recrystallisation from a tetrahydrofuran /ethyl ether mixture.

Using the same procedure the following compounds were prepared from the appropriate starting-products:

| Compound | Melting point °C |
| --- | --- |
| 2-(4-Benzofuryloxy)-butyramidoxime hydrochloride | 141–143 |
| 2-(6-Benzofuryloxy)-butyramidoxime hydrochloride | 149–152 |
| 2-(6-Benzofuryloxy)-propionamidoxime hydrochloride | 170–174 |
| 2-(5-Benzofuryloxy)-propionamidoxime hydrochloride | 164–166 |
| 2-(5-Benzofuryloxy)-butyramidoxime hydrochloride | 167–171 |

-continued

| Compound | Melting point °C |
| --- | --- |
| 2-(2,3-Dimethyl-5-benzofuryloxy)-propionamidoxime hydrochloride | 188–194 |
| 2-(2,3-Dimethyl-5-benzofuryloxy)-butyramidoxime acid oxalate | 153–156 |
| 2-(2,3-Dimethyl-6-benzofuryloxy)-butyramidoxime hydrochloride | 180–184 |
| 2-[(1,4-Benzodioxanyl)-5-oxy]-butyramidoxime hydrochloride | 178–181 |
| 2-(1-Naphthyloxy)-butyramidoxime hydrochloride | 178–181 |
| 2-(2-Naphthyloxy)-butyramidoxime | 97–101 |
| 2-(2,3-Dimethyl-6-benzofuryloxy)-propionamidoxime hydrochloride | 199–203 |

EXAMPLE 3

Preparation of 2-(2,3-Dimethyl-4-benzofuryloxy)-acetamidoxime hydrochloride a) (2,3-Dimethyl-4-benzofuryloxy)-acetonitrile To a solution of 19 g (0.117 mol) of 2,3-dimethyl-4-hydroxbenzofuran in 100 ml of methyl ethyl ketone, were added 16.1 g (0.117 mol) of finely divided anhydrous potassium carbonate. Under vigorous stirring the suspension was refluxed for 30 minutes and then allowed to cool to room temperature. After which a mixture of 9.1 g (0.12 mol) of chloracetonitrile and 0.3 g of potassium iodide in 15 ml of methyl ethyl ketone was added drop-by-drop and while stirring.

The reaction medium was refluxed for 2 hours, allowed to cool and the inorganic salts were filtered off. The filtrate was evaporated to dryness under reduced pressure and the residue so obtained was taken up in ether. The ethereal solution was washed with a 5 % sodium hydroxide solution and then with distilled water. The mixture was then dried over anhydrous sodium sulphate and fractionated by distillation.

The fraction distilling between 124° and 130° C under 0.5 mm.Hg was (2,3-dimethyl-4-benzofuryloxy)acetonitrile which was crystallised from a n-hexane/ethanol mixture.

In this manner, 18.3 g of (2,3-dimethyl-4-benzofuryloxy)-acetonitrile were obtained, melting at 50°–52° C which represents a yield of 78 % of the theoretical value.

By following the same procedure as that decribed above but using the appropriate starting-products, the compounds listed hereunder were prepared:

| Compound | Boiling point °C |
| --- | --- |
| (2,3-Dimethyl-6-benzofuryloxy)-acetonitrile M.P. 42–45°C | 126–129 (0.4 mm.Hg) |
| (2,3-Dimethyl-5-benzofuryloxy)-acetonitrile | M.P. 78–80°C |
| (6-Benzofuryloxy)-acetonitrile | 98–100 (0.15 mm.Hg) |
| $n_D^{26} = 1.5650$ 2-(4-Benzofuryloxy)-propionitrile | 88–94 (0.4 mm.Hg) |
| $n_D^{27} = 1.5438$ 2-[(1,4-Benzodioxanyl)-5-oxy]-propionitrile 2-(1-Naphthyloxy)-propionitrile | M.P. 65–67°C 115–117 (0.2 mm.Hg) |
| $n_D^{27} = 1.5863$ 2-(2-Naphthyloxy)-propionitrile | 135–138 (0.2 mm.Hg) |
| (prepared in dimethylformamide for 6 hours at 90°C) $n_D^{24} = 1.5880$ | |

-continued

| Compound | Boiling point °C |
|---|---|
| (5-Benzofuryloxy)-acetonitrile | 87–94 |
| $n_D^{25} = 1.5649$ | (0.1 mm.Hg) |
| (2,3-Dihydro-7-benzofuryloxy)-acetonitrile | 98–104 |
| M.P. 50–53°C | (0.2 mm.Hg) |
| (4-Benzothienyloxy)-acetonitrile | 102–104 |
| $n_D^{26} = 1.6172$ | (0.15 mm.Hg) |
| 2-(4-Benzothienyloxy)-propionitrile | 110–113 |
| $n_D^{32} = 1.5913$ | (0.25 mm.Hg) | b) (2,3-Dimethyl-4-benzofuryloxy)-acetamidoxime hydrochloride

This compound was obtained in accordance with the method described in Example 1 (d) starting from (2,3-dimethyl-4-benzofuryloxy)-acetonitrile. M.P. of the hydrochloride 185°–189° C after recrystallisation from isopropanol.

Using the same procedure, the following compounds were prepared from the appropriate starting-products:

| Compound | Melting point °C |
|---|---|
| 2-(2,3-Dimethyl-6-benzofuryloxy)-acetamidoxime hydrochloride | 180–184 |
| 2-(2,3-Dimethyl-5-benzofuryloxy)-acetamidoxime hydrochloride | 185–187 |
| 2-(6-Benzofuryloxy)-acetamidoxime hydrochloride | 150–154 |
| 2-(4-Benzofuryloxy)-propionamidoxime hydrochloride | 170–173 |
| 2-[(1,4-Benzodioxanyl)-5-oxy]-propionamidoxime hydrochloride | 135–139 |
| 2-(1-Naphthyloxy)-propionamidoxime | 116–119 |
| 2-(1-Naphthyloxy)-propionamidoxime hydrochloride | 190–191 |
| 2-(2-Naphthyloxy)-propionamidoxime hydrochloride | 172–175 |
| 2-(2-Methyl-5-benzofuryloxy)-acetamidoxime hydrochloride | 173–175 |
| 2-(2,3-Dimethyl-7-benzofuryloxy)-acetamidoxime hydrochloride | 164–167 |
| 2-(7-Benzofuryloxy)-acetamidoxime hydrochloride | 164–167 |
| 2-(5-Benzofuryloxy)-acetamidoxime hydrochloride | 179–183 |
| 2-(2,3-Dihydro-7-benzofuryloxy)-acetamidoxime | 155–158 |
| 2-(4-Benzothienyloxy)-acetamidoxime | 166–168 |
| 2-(4-Benzothienyloxy)-propionamidoxime hydrochloride | 200–203 |

EXAMPLE 4

Preparation of 2-(1-naphthyloxy)-2-methyl-propionamidoxime hydrochloride a) 2-(1-Naphthyloxy)-2-methyl-propionitrile

To a suspension of 22.9 g (0.1 mol) of 2-(1-naphthyloxy)-2-methyl-propionamide in 50 ml of anhydrous pyridine were added, drop-by-drop and under vigorous stirring, 23 g (0.15 mol) of phosphorus oxychloride. During this operation the temperature was maintained below 70° C.

Stirring was maintained for 24 hours at room temperature and the reaction medium was poured onto crushed ice. After extraction with ether the ethereal phase so obtained was successively washed with water, with acidified water and finally with water. The mixture was dried over anhydrous sodium sulphate, the solvent was evaporated and the residue obtained was distilled under high vacuum.

In this manner 17.7 g of 2-(1-naphthyloxy)-2-methyl-propionitrile were obtained, boiling at 115°–120° C under 0.3 mm Hg which represents a yield of 84 %.

$n_D^{25} = 1.5729$

By following the same procedure as that described above but using the appropriate starting-products, the following compounds were prepared:

| Compound | Boiling point °C |
|---|---|
| 2-(2,3-Dimethyl-6-benzofuryloxy)-2-methyl-propionitrile | 108–110 |
| $n_D^{26} = 1.5300$ | (0.3 mm.Hg) |
| 2-(2,3-Dihydro-7-benzofuryloxy)-propionitrile | 102–104 |
| $n_D^{30} = 1.5287$ | (0.2 mm.Hg) |
| 2-(2-Naphthyloxy)-2-methyl-propionitrile | 105–112 |
| $n_D^{24} = 1.5730$ | (0.2 mm.Hg) |
| 2-(1-Napthyloxy):valeronitrile | 144–145 |
| $n_D^{27} = 1.5705$ | (0.5 mm.Hg) |
| 2-(7-Benzofuryloxy)-valeronitrile | 130–132 |
| $n_D^{26} = 1.5312$ | (0.7 mm.Hg) | b) 2-(1-Naphthyloxy)-2-methyl-propionamidoxime hydrochloride

This compound was obtained in accordance with the method described in Example 1 (d) starting from 2-(1-naphthyloxy)-2-methyl-propionitrile M.P. 180°–183° C after recrystallisation from isopropanol.

By following the same procedure the following compounds were prepared using the appropriate starting-products:

| Compound | Melting point °C |
|---|---|
| 2(2,3-Dimethyl-6-benzofuryloxy)-2-methyl-propionamidoxime hydrochloride | 159–162 |
| 2-(2,3-Dihydro-7-benzofuryloxy)-propionamidoxime hydrochloride | 184–187 |
| 2-(2-Napthloxy)-2-methyl-propionamidoxime hydrochloride | 155–158 |
| 2-(1-Naphthyloxy)-valeramidoxime hydrochloride | 193–196 |
| 2-(7-Benzofuryloxy)-valeramidoxime hydrochloride | 157–160 |

EXAMPLE 5

Preparation of 2-(7-benzofuryloxy)-propionamidoxime hydrochloride

A mixture of 51.25 g (0.25 mol) of 2-(7-benzofuryloxy)-propionamide, 76 g of thionyl chloride and 200 ml of dry benzene was refluxed for 5 hours. The mixture was then allowed to stand for 15 hours at room temperature and then poured onto ice.

The organic phase was washed with water, then with a diluted solution of sodium carbonate and finally with water. After the mixture was dried and the solvent evaporated, the residue was distilled and 29.3 g of 2-(7-benzofuryloxy)-propionitrile were obtained, boiling at 118° C under 0.4 mm. Hg, ($n_D^{24}$ = 1.5440) which represents a yield of 62 % of the theoretical value. This nitrile was treated following the method described in Example 1 (d) to obtain 2-(7-benzofuryloxy)propionamidoxime melting at 92°–94° C after recrystallisation from a hexane/isopropyl mixture.

M.P. of the hydrochloride: 178°–181° C (from isopropanol)

EXAMPLE 6

Preparation of
3-(2-methyl-5-benzofuryloxy)-propionamidoxime hydrochloride a) 3-(2-Methyl-5-benzofuryloxy)-propionitrile A mixture of 59.2 g (0.4 mol) of 2-methyl-5-hydroxy-benzofuran, 32 g (0.6 mol) of acrylonitrile, 4 g of monohydrated cupric acetate, 5 ml of acetic acid and 5 ml of acetic anhydride were heated for 6 hours at 95° C.

The volatile fractions were evaporated out under vacuum and the residue obtained was taken up in ether. The ethereal phase was washed with a diluted solution of sodium hydroxide and then with water. The mixture was dried on anhydrous sodium sulphate, the solvent was evaporated out and the residue was recrystallised from cyclohexane.

In this manner, 27 g of 3-(2-methyl-5-benzofuryloxy)-propionitrile were obtained melting at 73°–76° C which represents a yield of 33.5 %.

By following the same procedure as that described above, the following compounds were prepared in the presence of trimethylbenzylammonium hydroxide in place of cupric acetate and without acetic acid and acetic anhydride:

| Compound | Melting point ° |
|---|---|
| 3-(7-Benzofuryloxy)-propionitrile | 49–50 |
| 3-(2,3-Dimethyl-5-benzofuryloxy)-propionitrile | 72–74 |
| 3-(4-Benzothienyloxy)-propionitrile | 70–71 |
| 3-[(1,4-Benzodioxanyl)-5-oxyl-propionitrile | 73–75 |
| 3-(4-Benzofuryloxy)-propionitrile $n_D^{26.5}$ = 1.5561 | B.P. 101–102°C (0.09 mm.Hg) |
| 3-(2,3-Dihydro-7-benzofuryloxy)-propionitrile $n_D^{28}$ = 1.5460 | B.P. 120–122°C (0.25 mm.Hg) |
| 3-(6-Benzofuryloxy)-propionitrile | 80–81 | b) 3-(2-Methyl-5-benzofuryloxy)-propionamidoxime hydrochloride

This compound was obtained in accordance with the procedure described in Example 1 (d) starting from 3-(2-methyl-5-benzofuryloxy)-propionitrile.

M.P. 163°–167° C after recrystallisation from isopropanol.

By following the same method, the compounds hereunder were prepared using the appropriate starting-products:

| Compound | Melting point °C |
|---|---|
| 3-(7-Benzofuryloxy)-propionamidoxime hydrochloride | 133–138 |
| 3-(2,3-Dimethyl-5-benzofuryloxy)-propionamidoxime hydrochloride | 162–164 |
| 3-(4-Benzothienyloxy)-propionamidoxime hydrochloride | 164–167 |
| 3-(1-Naphthyloxy)-propionamidoxime hydrochloride | 169–173 |
| 3-(2-Naphthyloxy)-propionamidoxime hydrochloride | 171–174 |
| 3-[(1,4-Benzodioxanyl)-5-oxy]-propionamidoxime hydrochloride | 181–184 |
| 3-(4-Benzofuryloxy)-propionamidoxime hydrochloride | 164–167 |
| 3-(2,3-Dihydro-7-benzofuryloxy)-propionamidoxime hydrochloride | 153–155 (decomposition) |
| 3-(6-Benzofuryloxy)-propionamidoxime hydrochloride | 166–169 |

EXAMPLE 7

Preparation of
2-(2-methyl-3-benzofuryloxy)-acetamidoxime hydrochloride a) (2-Methyl-3-benzofuryloxy)-acetonitrile While stirring 14.8 g (0.1 mol) of 2-methyl-3-hydroxy-benzofuran were added drop-by-drop and at room temperature, to a suspension of 6 g of sodium hydride (50 % in oil) in 100 ml of dimethylformamide. The mixture was stirred for a further 20 minutes and then 15.1 g (0.2 mol) of chloracetonitrile were added.

Stirring was maintained for 48 hours after which the reaction medium was poured into water and extracted with ether.

In this manner 12 g of (2-methyl-3-benzofuryloxy)-acetonitrile boiling at 100°–104° C under 0.15 mm.Hg and melting at 58°–60° C after recrystallisation from petroleum ether (40°–80° C) were obtained.

By following the same procedure as that described above but using the appropriate starting-products, the compounds listed hereunder were prepared:

| Compound | Boiling point °C |
|---|---|
| (2-Ethyl-3-benzofuryloxy)-acetonitrile M.P. 37–43°C | 118–122 (0.5 mm.Hg) |
| 3-(2-Ethyl-3-benzofuryloxy)-propionitrile | M.P. 63–65°C |
| (2-Isopropyl-3-benzofuryloxy)-acetonitrile $n_D^{25}$ = 1.5328 | 98–105 (0.1 mm.Hg) |
| 3-(2-Methyl-3-benzofuryloxy)-propionitrile $n_D^{25}$ = 1.5518 | 120–125 (0.1 mm.Hg) |
| 3-(2-Isopropyl-3-benzofuryloxy)-propionitrile $n_D^{25}$ = 1.4610 | 120–130 (0.2 mm.Hg) |
| 4-(4-Benzofuryloxy)-butyronitrile $n_D^{30}$ = 1.4623 | 130–135 (0.45 mm.Hg) |
| 4-(7-Benzofuryloxy)-butyronitrile $n_D^{27}$ = 1.5512 | 158–160 (0.5 mm.Hg) |

The following compounds were prepared in accordance with the method described hereabove but using 2-benzenesulphonyloxy-butyronitrile as starting-compound:

| Compound | Boiling point °C |
|---|---|
| 2-(2-Methyl-3-benzofuryloxy)-butyronitrile | 102–106 (0.2 mm.Hg) |
| $n_D^{24} = 1.5268$ | |
| 2-(2-Ethyl-3-benzofuryloxy)-butyronitrile | 110–117 (0.2 mm.Hg) |
| $n_D^{24} = 1.5242$ | |
| 2-(2-Isopropyl-3-benzofuryloxy)-butyronitrile | 105–110 (0.1 mm.Hg) |
| $n_D^{24} = 1.5192$ | | b) 2-(2-Methyl-3-benzofuryloxy)-acetamidoxime hydrochloride

This compound was obtaind in accordance with the method described in Example 1 (d) starting from (2-methyl-3-benzofuryloxy)acetonitrile.

M.P. 183°–187° C after recrystallisation from an ethyl acetate/methanol mixture.

By following the same procedure the following compounds were prepared starting from the appropriate compounds:

| Compound | Melting point °C |
|---|---|
| 2-(2-Ethyl-3-benzofuryloxy)-acetamidoxime | 144–146 |
| 2-(2-Ethyl-3-benzofuryloxy)-acetamidoxime acid oxalate | 160–161 |
| 2-(2-Methyl-3-benzofuryloxy)-butyramidoxime | 138–140 |
| 2-(2-Methyl-3-benzofuryloxy)-butyramidoxime hydrochloride | 170–174 |
| 2-(2-Ethyl-3-benzofuryloxy)-butyramidoxime | 139–141 |
| 2-(2-Isopropyl-3-benzofuryloxy)-butyramidoxime | 154–157 |
| 3-(2-Ethyl-3-benzofuryloxy)-propionamidoxime | 120–122 |
| 3-(2-Ethyl-3-benzofuryloxy)-propionamidoxime hydrochloride | 160–163 |
| 2-(2-Isopropyl-3-benzofuryloxy)-acetamidoxime | 165–167 |
| 2-(2-Isopropyl-3-benzofuryloxy)-acetamidoxime acid oxalate | 171–173 |
| 3-(2-Methyl-3-benzofuryloxy)-propionamidoxime acid oxalate | 173–176 |
| 3-(2-Isopropyl-3-benzofuryloxy)-propionamidoxime | 158–160 |
| 3-(2-Isopropyl-3-benzofuryloxy)-propionamidoxime hydrochloride | 180–183 |
| 4-(4-Benzofuryloxy)-butyramidoxime hydrochloride | 183–186 |
| 4-(7-Benzofuryloxy)-butyramidoxime acid oxalate | 145–147 |

EXAMPLE 8

Preparation of 2-(2-methyl-3-benzofuryloxy)-2-methyl-propionamidoxime hydrochloride a) Methyl 2-(2-methyl-3-benzofuryloxy)-2-methyl-propionate

To a suspension of 9 g of sodium hydride (50 % in oil) in 150 ml of anhydrous dimethylformamide were added drop-by-drop and while stirring 22.2 g (0.15 mol) of 2-methyl-3-hydroxy-benzofuran, care being taken to maintain the temperature at about 30°–35° C. The reaction medium was stirred for a further 15 minutes and then 27.2 g (0.15 mol) of methyl α-bromoisobutyrate were added, the temperature being maintained at 35°–40° C. Stirring was continued for 24 hours at room temperature, the reaction mixture was poured into water and extracted several times with ether. The ethereal extracts were collected, washed with water and dried over anhydrous sodium sulphate. The solvent was evaporated under vacuum and the residue was distilled.

In this manner 22.3 g of methyl 2-(2-methyl-3-benzofuryloxy)-2-methyl-propionate were obtained boiling at 110°–115° C under 0.2 mm. Hg which represents a yield of 60 % of the theoretical value.

By following the same procedure as that described above but using the appropriate starting-products, the following compounds were prepared:

| Compound | Boiling point °C |
|---|---|
| Methyl 2-(2-ethyl-3-benzofuryloxy)-2-methyl-propionate | 116–120 (0.2 mm.Hg) |
| $n_D^{24} = 1.5220$ | |
| Methyl 2-(2-isopropyl-3-benzofuryloxy)-2-methyl-propionate | 103–106 (0.1 mm.Hg) |
| $n_D^{25} = 1.5180$ | |
| Ethyl 2-(2-Isopropyl-3-benzofuryloxy)-propionate | 64–67 (0.05 mm.Hg) |
| $n_D^{24} = 1.5235$ | |
| Ethyl 2-(2-ethyl-3-benzofuryloxy)-propionate | 65–70 (0.1 mm.Hg) |
| $n_D^{26} = 1.5427$ | |
| Ethyl 2-(2-methyl-3-benzofuryloxy)-propionate | 105–110 (0.2 mm.Hg) |
| $n_D^{23} = 1.5162$ | | b) 2-(2-Methyl-3-benzofuryloxy)-2-methyl-propionamide

A solution of 24.8 g (0.1 mol) of methyl 2-(2-methyl-3-benzofuryloxy)-2-methyl-propionate in 400 ml of methanol saturated with ammonia was allowed to stand for 8 days at room temperature. The solvent was evaporated under vacuum and the residue was crystallised from petroleum ether (40°–80° C).

In this manner, 13.1 g of 2-(2-methyl-3-benzofuryloxy)-2-methyl-propionamide were obtained melting at 116°–120° C which represents a yield of 56 % of the theoretical value.

By following the procedure described above but using the appropriate starting-products, the following compounds were prepared:

| Compound | Melting point °C |
|---|---|
| 2-(2-Ethyl-3-benzofuryloxy)-2-methyl-propionamide | 82–84 |
| 2-(2-Isopropyl-3-benzofuryloxy)-2-methyl-propionamide | 104–105 |
| 2-(2-Isopropyl-3-benzofuryloxy)-propionamide | 110–113 |
| 2-(2-Ethyl-3-benzofuryloxy)-propionamide | 100–103 |
| 2-(2-Methyl-3-benzofuryloxy)-propionamide | 145–148 | c) 2-(2-Methyl-3-benzofuryloxy)-2-methyl-propionitrile

This compound was obtained in accordance with the method described in Example 4 (a) starting from 2-(2-methyl-3-benzofuryloxy)-2-methyl-propionamide.

B.P. 95°–100° C under 0.2 mm.H.g.

M.P. 53°–55° C after recrystallisation from petroleum ether (50°–75° C).

By following the same procedure the compounds listed hereunder were obtained:

| Compound | Boiling point °C |
|---|---|
| 2-(2-Ethyl-3-benzofuryloxy)-2-methyl-propionitrile | 100–108 (0.2 mm.Hg) |
| $n_D^{24} = 1.5238$ | |
| 2-(2-Isopropyl-3-benzofuryloxy)-2-methyl-propionitrile | 103–108 (0.15 mm.Hg) |
| $n_D^{24} = 1.5240$ | |
| 2-(2-Isopropyl-3-benzofuryloxy)-propionitrile | 96–99 (0.1 mm.Hg) |
| $n_D^{25} = 1.5258$ | |
| 2-(2-Ethyl-3-benzofuryloxy)-propionitrile | 108–110 (0.2 mm.Hg) |
| $n_D^{24} = 1.5291$ | |
| 2-(2-Methyl-3-benzofuryloxy)-propionitrile | 95–98 (0.25 mm.Hg) |
| $n_D^{25} = 1.5298$ | | d)

2-(2-Methyl-3-benzofuryloxy)-2-methyl-propionamidoxime hydrochloride

This compound was prepared in accordance with the method described in Example 1 (d) starting from 2-(2-methyl-3-benzofuryloxy)-2-methyl-propionitrile. M.P. 162°–166° C.

By following the same procedure the compounds listed hereunder were prepared:

| Compound | Melting point °C |
|---|---|
| 2-(2-Ethyl-3-benzofuryloxy)-2-methyl-propionamidoxime hydrochloride | 147–150 |
| 2-(2-Isopropyl-3-benzofuryloxy)-2-methyl-propionamidoxime hydrochloride | 165–168 |
| 2-(2-Isopropyl-3-benzofuryloxy)-propionamidoxime | 137–140 |
| 2-(2-Ethyl-3-benzofuryloxy)-propionamidoxime | 103–106 |
| 2-(2-Ethyl-3-benzofuryloxy)-propionamidoxime hydrochloride | 137–140 |
| 2-(2-Methyl-3-benzofuryloxy)-propionamidoxime | 121–123 |
| 2-(2-Methyl-3-benzofuryloxy)-propionamidoxime acid oxalate | 146–148 |

EXAMPLE 9

Hard-gelatin capsules containing the following ingredients were prepared in accordance with known pharmaceutical technique:

| | Ingredient | mg per capsule |
|---|---|---|
| a) | 2-(7-Benzofuryloxy)-propionamidoxime hydrochloride | 10 |
| | Microcrystalline cellulose | 110 |
| | | 120 |
| b) | 2-(7-Benzofuryloxy)-propionamidoxime hydrochloride | 10 |
| | Starch | 190 |
| | | 200 |
| c) | 2-(1-Naphthyloxy)-propionamidoxime hydrochloride | 5 |
| | Microcrystalline cellulose | 115 |
| | | 120 |
| d) | 2-(1-Naphthyloxy)-propionamidoxime hydrochloride | 5 |
| | Starch | 195 |
| | | 200 |
| e) | 2-(1-Naphthyloxy)-propionamidoxime hydrochloride | 15 |
| | Starch | 185 |
| | | 200 |

We claim:

1. An amidoxime derivative corresponding to the general formula:

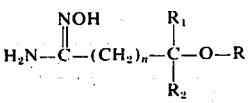

or a pharmaceutically acceptable acid addition salt thereof, wherein $R_1$ and $R_2$, which are the same or different, represent hydrogen or a straight-chain lower alkyl radical containing from 1 to 3 carbon atoms, n is 0, 1 or 2 and R is naphthyl,
   a. when n is 1, $R_1$ and $R_2$ are each hydrogen;
   b. when n is 2, $R_1$ and $R_2$ are each hydrogen and R is β-naphthyl.

2. 2-(1-Naphthyloxy)-propionamidoxime or a pharmaceutically acceptable acid addition salt thereof.

3. 2-(1-Naphthyloxy)-butyramidoxime or a pharmaceutically acceptable acid addition salt thereof.

4. 3-(2-Naphthyloxy)-propionamidoxime or a pharmaceutically acceptable acid addition salt thereof.

* * * * *